(12) United States Patent
Bächler et al.

(10) Patent No.: US 9,993,318 B2
(45) Date of Patent: Jun. 12, 2018

(54) RETENTION INSERT AND CONNECTION DEVICE FOR DENTAL APPLICATIONS

(71) Applicant: VALOC AG, Mohlin (CH)

(72) Inventors: Martin Bächler, Oberdorf (CH); Jürg Bächler, Hölstein (CH); Roland Schaffner, Liestal (CH)

(73) Assignee: VALOC AG, Mohlin (CH)

( * ) Notice: Subject to any disclaimer, the term of this patent is extended or adjusted under 35 U.S.C. 154(b) by 284 days.

(21) Appl. No.: 14/401,914

(22) PCT Filed: May 17, 2013

(86) PCT No.: PCT/EP2013/060224
§ 371 (c)(1),
(2) Date: Jan. 23, 2015

(87) PCT Pub. No.: WO2013/174738
PCT Pub. Date: Nov. 28, 2013

(65) Prior Publication Data
US 2015/0140512 A1    May 21, 2015

(30) Foreign Application Priority Data
May 21, 2012 (EP) .................... 12168613

(51) Int. Cl.
*A61C 13/12*    (2006.01)
*A61C 13/225*    (2006.01)
(Continued)

(52) U.S. Cl.
CPC ........ *A61C 8/0062* (2013.01); *A61C 13/2656* (2013.01)

(58) Field of Classification Search
CPC .... A61C 5/00; A61C 5/08; A61C 8/00; A61C 8/0048; A61C 8/005–8/0059;
(Continued)

(56) References Cited

U.S. PATENT DOCUMENTS 4,549,319 A * 10/1985 Meyer .................. A61C 8/0018
606/100
4,756,689 A * 7/1988 Lundgren .............. A61C 8/005
433/169

(Continued)

FOREIGN PATENT DOCUMENTS

DE    1491045 A1    7/1969
DE    19508771 A1    9/1995
(Continued)

OTHER PUBLICATIONS

International Search Report for International Application No. PCT/EP2013/060224 dated Aug. 2, 2013.
(Continued)

*Primary Examiner* — Stephen R Crow
*Assistant Examiner* — Garrett Atkinson
(74) *Attorney, Agent, or Firm* — Kratz, Quintos & Hanson, LLP

(57) ABSTRACT

A retention insert (1), for connecting a dental prosthesis structure to a dental implant or capping structure having a head designed for a press-fit connection, comprises a substantially circular disc-shaped end face (12), and a substantially ring-shaped retention edge (11), which protrudes from the end face (12) and has an outer surface (114). The end face (12) has an opening (121), and, starting from an end (11*b*) of the retention edge (11) directed away from the end face (12), a substantially axial slit (14) extends through the retention edge (11) and the end face (12) to the opening (121) of the end face (12). Connected to the opening on the end face, the slit of the retention insert according to the invention is a relatively simple structure which ensures that the retention insert, and in particular the retention edge thereof, has an elasticity sufficient for snap-fitting it onto the head or the patrix head. At the same time, a spring force from the snapped-on retention edge can therefore act on the head, (Continued)

such that the retention insert and parts connected thereto are clamped on the head. Moreover, this retention edge and this opening also have the result that imprecisions in the position of the implant structure, and in particular lack of parallelism, and also the effects of forces from different directions can be compensated, without the retention insert or parts thereof being substantially squeezed or similarly deformed.

15 Claims, 2 Drawing Sheets

(51) Int. Cl.
*A61C 8/00* (2006.01)
*A61C 13/265* (2006.01)

(58) Field of Classification Search
CPC ..... A61C 8/006–8/0069; A61C 8/007–8/0078; A61C 13/2656
USPC ................. 433/172–179, 191–195, 218–221
See application file for complete search history.

(56) References Cited

U.S. PATENT DOCUMENTS

| | | | | |
|---|---|---|---|---|
| 4,854,872 A * | 8/1989 | Detsch | ................. | A61C 8/0001 433/173 |
| 4,856,994 A * | 8/1989 | Lazzara | ................. | A61C 8/00 433/173 |
| 4,988,298 A * | 1/1991 | Lazzara | ................. | A61C 8/005 433/173 |
| 5,026,285 A * | 6/1991 | Durr | ................. | A61C 8/005 433/141 |
| 5,125,839 A * | 6/1992 | Ingber | ................. | A61C 8/0001 433/169 |
| 5,209,659 A * | 5/1993 | Friedman | ................. | A61C 8/0018 433/173 |
| 5,211,561 A * | 5/1993 | Graub | ................. | A61C 8/0086 433/169 |
| 5,344,457 A * | 9/1994 | Pilliar | ................. | A61C 8/0012 433/174 |
| 5,527,182 A * | 6/1996 | Willoughby | ................. | A61C 8/0001 433/172 |
| 5,873,721 A * | 2/1999 | Willoughby | ................. | A61C 8/0001 433/172 |
| 5,890,902 A | 4/1999 | Sapian | | |
| 6,273,720 B1 * | 8/2001 | Spalten | ................. | A61C 8/0009 433/172 |
| 6,283,753 B1 * | 9/2001 | Willoughby | ................. | A61C 8/0001 433/172 |
| 7,293,991 B1 * | 11/2007 | Karapetyan | ................. | A61C 8/005 433/173 |
| 8,454,363 B2 * | 6/2013 | Worthington | ................. | A61C 8/0001 433/174 |
| 8,583,270 B2 * | 11/2013 | Schneider | ................. | A61C 8/0077 700/118 |
| 8,778,443 B2 * | 7/2014 | Uckelmann | ................. | A61C 1/0061 427/2.26 |
| 2003/0224329 A1 * | 12/2003 | Carlton | ................. | A61C 8/005 433/173 |
| 2004/0005530 A1 | 1/2004 | Mullaly | | |
| 2006/0194171 A1 * | 8/2006 | Lazarof | ................. | A61C 8/0033 433/173 |
| 2009/0306777 A1 * | 12/2009 | Widmer | ................. | A61B 17/0401 623/13.14 |
| 2012/0003606 A1 * | 1/2012 | Fischler | ................. | A61C 8/0048 433/141 |
| 2014/0302457 A1 * | 10/2014 | Siegmund | ................. | A61C 13/20 433/173 |

FOREIGN PATENT DOCUMENTS

| | | | |
|---|---|---|---|
| EP | 0298286 A1 | 1/1989 | |
| EP | 0 894 480 A1 | 2/1999 | |
| EP | 1021999 A1 | 7/2000 | |
| EP | 2 248 485 A1 | 11/2010 | |
| EP | 2248485 A1 * | 11/2010 | ........... A61C 8/0001 |
| FR | 2654330 A1 | 5/1991 | |
| FR | 2689387 A1 | 10/1993 | |
| FR | 2799950 A1 | 4/2001 | |
| GB | 300596 A | 5/1928 | |
| JP | 2000-217842 A | 8/2000 | |
| WO | 2006105684 A1 | 10/2006 | |
| WO | 2009127877 A1 | 10/2009 | |
| WO | WO 2011/027229 A2 | 3/2011 | |

OTHER PUBLICATIONS

European Notice of Opposition proceedings against EP 2 852 350 B1 (Nobel Biocare Services AG (CH)) (18 Sheets).

Dr. Robert Laux; ZWL Zahntechnik Wirtschaft Labor; Issue 3; Jun. 2011; pp. 1 and 31-33 (4 Sheets, 3 Sheets translation, 7 Sheets total).

Catalogue Cendres+Métaux SA; 2010; 1 Sheet entitled Brief/Fax Kataloge 2010 and pp. 1, 46-47 and 162 (5 Sheets, 4 Sheets translation, 9 Sheets total).

* cited by examiner

RETENTION INSERT AND CONNECTION DEVICE FOR DENTAL APPLICATIONS

TECHNICAL FIELD

The invention relates to a retention insert according to the preamble of independent claim 1, and to an associated connection device.

Retention inserts with a substantially circular disk-shaped end face, and with a substantially ring-shaped retention edge which protrudes from the end face and has an outer surface, wherein the end face and the retention edge form a recess with an inner surface, which is designed corresponding to an outer surface of a head of a dental implant structure or capping structure, such that, by arranging the head in the recess, the retention insert can be snap-fitted onto the head, can be used for connecting a dental prosthesis structure to the dental implant structure or capping structure.

PRIOR ART

In dentistry, damaged or diseased teeth are nowadays generally replaced. by an artificial denture. Implants are often inserted as root replacements into a law bone of a patient. An abutment is then fitted partially onto the implant, wherein the implant itself, or the longitudinal end of the abutment directed away from the implant, is designed with a connecting arrangement, on which a prosthesis structure can be mounted. In a widely used configuration, this connecting arrangement is designed as a press-fit connection, wherein typically a male part of the press-fit connection, i.e. the patrix, is formed on the abutment or implant, and a female part of the press-fit connection, i.e. the matrix, is connected to the prosthesis structure.

WO 2010025034 A1, example, describes a dental anchoring device comprising a patrix head, formed on the abutment or directly on the implant, and a matrix housing, which is securely connected to the prosthesis structure. The matrix moreover comprises a retention insert, which is fitted into the matrix housing before the matrix is snap-fitted, together with the prosthesis structure, onto the patrix head. The patrix head has a flat head end, and an outer surface curving outward in a convex shape and acting as a snap-fit surface. In the flat head end, an opening with an inner profile is let into the patrix head, through which opening, on the one hand, a screwing tool can engage for screwing the abutment or the implant and, on the other hand, a punch or stopper can clamp the retention insert.

Another press-fit connection system is described in WO 2011/027229 A2. Here, the matrix is refined, inter alia, such that the retention insert is securely connected to the matrix housing via a locking mechanism when the matrix is snap-fitted onto the patrix. Moreover, the retention insert has a retention edge with several lamellae for ensuring an elasticity sufficient to snap-fit onto the patrix head and for compensating for uneven forces acting on the matrix, for example during chewing movements. The shape of the lamellae of the retention edge can also determine the pulling-off or holding force of the retention insert and, therefore, of a prosthesis structure connected to it.

The object of the following invention is to propose an alternative retention insert and an alternative connection device suitable for a press-fit connection system, which permit an efficient and lasting connection of a prosthesis structure to a law bone and permit reliable handling when fitting and removing the prosthesis structure.

DISCLOSURE OF THE INVENTION

According to the invention, the object is achieved by a retention insert as defined in independent claim 1 and by a connection device as defined in independent claim 9. Advantageous variants of the invention are set forth in the dependent claims.

The core of the invention is the following: A retention insert, for connecting a dental prosthesis structure to a dental implant structure or capping structure, that has a head designed for a press-fit connection, comprises a substantially circular disk-shaped end face, and a substantially ring-shaped retention edge, which protrudes from the end face and has an outer surface. The end face and the retention edge form a recess with an inner surface, which is designed corresponding to an outer surface of the head of the dental implant structure or capping structure, such that, by arranging the head of the implant structure or capping structure in the recess of the retention insert, the retention insert can be snap-fitted onto the head of the implant structure or capping structure. The retention insert, with its end face closing the retention edge, can thus be substantially cup-shaped, which can be advantageous for reversible snap-fitting onto the head, or which may indeed permit such a snap-fitting. In particular, the end face can close the retention edge to the extent that an interior enclosed by the retention edge is axially closed or is delimited by at least partial covering. For example, the end face can form a bottom or a top on which the head engages when snap-fitted and which thus limits a snap movement of the retention insert. The retention edge can engage around the head and hold the retention insert on the head. The end face has an opening, and, starting from an end of the retention edge directed away from the end face, a substantially axial slit extends through the retention edge and the end face to the opening of the end face.

In connection with the slit, the term "axial" is to be understood as a longitudinal axis of the retention insert extending from the end face in the direction of the end of the retention edge directed away from the end face. In the case of a plane end face, the longitudinal axis can typically be at a right angle to the end face and extend centrally through the retention insert. In use, for the snap-fitting, the head of the implant structure or capping structure is normally guided along the longitudinal axis into the recess of the retention insert.

The term "implant structure or capping structure" is to be understood, in connection with the invention, as any desired structure that is firmly connected to the jaw bone and that comprises means for releasably securing the prosthesis structure. In particular, these may include one-part implants, for example with a patrix head, corresponding implant/abutment combinations or capped teeth. Although capped teeth are not always explicitly mentioned below, they are nonetheless included as an alternative when implant structures are mentioned.

In this connection, the term "prosthesis structure" is to be understood as meaning various structures that may be suitable according application, for example those known as replacements for a single tooth, part of a tooth or a whole tooth, bridges, crowns, hybrid or total prostheses.

The head of the dental implant structure or capping structure can in particular be a patrix head of a press-fit connection. Such patrix heads can typically comprise a snap-fit portion which be designed corresponding to a matrix and in particular to a recess of the retention insert thereof.

During use of the retention insert, the end face normally forms an occlusal end of the retention insert. By contrast, during use of the retention insert, the end directed away from the end face normally forms en apical end of the retention insert.

The parts of the overall prosthesis and implant device that protrude above the gingiva or gum into the oral space during use, and that are therefore visible from the outside, can be designated as a superstructure. For example, the superstructure can comprise the prosthesis structure, a matrix of a press-fit connection, which can comprise the retention insert and a matrix housing or a holding shell, and, in the case of a two-part design of the implant structure, an abutment or at least parts and in particular a patrix of the press-fit connection.

The slit of the retention insert according to the invention, connected to the opening of the end face, is a relatively simple structure which ensures that the retention insert, and in particular the retention edge thereof, has sufficient elasticity for snap-fitting onto the head or patrix head. At the same time, when the retention insert has been snap-fitted, a spring force from the retention edge can therefore act on the head, such that the retention insert and parts connected thereto are clamped on the head. Moreover, the retention edge of the retention insert can move back resiliently to its original position after it is removed from the head, such that the retention insert is sub lent to relatively little stress and can have a relatively long useful life. Finally, this retention edge and this opening also have the effect that inaccuracies in the position of the implant structure and in particular disparalielism and forces acting from different directions can be compensated for without the retention insert or parts thereof being substantially squeezed or similarly deformed.

Preferably, the slit of the retention insert is substantially straight. The slit and the retention insert can thus be produced in a relatively simple way. In particular, the slit can also extend substantially parallel to the longitudinal axis of the retention insert or can intersect the retention edge at right angles to the end face. Alternatively, the slit can also be designed widening out and/or arranged obliquely and/or it can extend in a spiral shape along the retention edge in the direction of the end face. The retention insert can also have a plurality of slits.

In a preferred embodiment, the opening of the end face is designed as a bore. The bore preferably describes a substantially circular cross section. This permits simple and expedient production of the retention insert. The end face of the retention insert can also have a plurality of openings, particularly if there are several slits.

In another preferred embodiment, the opening of the end face is slit-shaped. This permits an alternative simple and expedient production of the retention insert. For example, in an embodiment with one or more oblique or spiral-shaped slits, the corresponding provision of one or more slit-shaped openings in the end face of the retention insert permits a relatively simple and useful structure.

Preferably, the retention edge of the retention insert has a projection protruding substantially radially from the outer surface. This projection can in particular extend along substantially the entire circumference of the retention edge. With such a projection, it is possible, in a relatively simple way, to ensure that the retention insert is firmly connected to a matrix housing or a holding shell when the retention insert is arranged in the matrix housing or in the holding shell. In particular, the projection can act as part of a locking mechanism for blocking the retention insert in the holding shell or the matrix housing. With the retention insert blocked in this way, the configuration according to the invention with a slit and an opening in the end face can ensure that, despite the firm connection of the retention insert in the holding shell or in the matrix housing, there is sufficient flexibility to take up and compensate for non-axial forces. The retention insert, particularly for uses with such a locking mechanism, can thus permit long-lasting and convenient handling.

Preferably, the retention edge of the retention insert has an inner surface which is opposite the outer surface and which is rounded toward the end of the retention insert directed away from the end face. With such a rounded design of the retention edge, it is possible to ensure that, on the one hand, the connection device is centered when fitted onto the male part of the press-fit connection or the head of the implant structure and, on the other hand, a force is applied continuously to the retention edge during this fitting. After the fitting has been completed, this force still remains, such that the retention edge is pressed and moved outward from the head and, in this way, a permanent or rigid connection between retention insert and holding shell or matrix housing is possible.

Preferably, the retention insert is produced from a biocompatible polymer material, in particular from a polyether ether ketone. Other possible biocompatible materials are polyamides, for example polyhexamethylene adipic acid amide. Retention inserts of this kind can be produced easily. Moreover, such retention inserts can also be used in holistic medicine, in which there are specific requirements regarding the materials and in which, in particular, the use of titanium is not allowed.

A further aspect of the invention concerns a connection device for connecting a dental prosthesis structure to a dental implant structure or capping structure. The connection device comprises a holding shell with an end face and a substantially ring-shaped holding edge protruding therefrom, and a retention insert as described above. The holding edge and the end face of the holding shell form a recess in which the retention insert can be arranged such that an outer surface of the retention edge of the retention insert lies at least partially at a distance from and adjacent to an inner surface of the holding edge of the holding shell when the retention insert is arranged in the recess of the holding shell and when substantially no radial forces act on the holding edge of the holding shell and on the retention edge of the retention insert.

The connection device can be provided in particular as a female part or matrix of a press-fit connection. The term "holding shell" refers in particular to a housing of the matrix or to a matrix housing. The outer surface of the retention edge and the inner surface of the holding edge can have any suitable shape, for example a substantially plane shape or a substantially curved shape. During use of the connection device, the holding shell can be firmly connected to the prosthesis structure, for which purpose it can be cast, for example, in a synthetic prosthesis material. To permit a suitable connection to the prosthesis structure, the holding shell can also have suitable means such as one or more notches on its outer surface. The end face of the holding shell can be substantially circular disk-shaped and provided with an opening or, in particular, completely closed. The holding edge can protrude substantially at a right angle from the circumference of the end face of the holding shell.

Since the adjacent outer surface of the retention edge and inner surface of the holding edge are at least partially not in contact with each other but instead spaced apart from each other when substantially no radial forces act on the holding edge of the holding shell and on the retention edge of the retention insert, it is possible, among other things, to ensure that the retention insert is connected relatively loosely to the holding shell when the connection device has not yet been fitted onto the head of the implant structure. This loose connection is sufficient for holding the retention insert in the holding shell, so as to allow comfortable handling. This loose connection can also allow the retention insert to be relatively easily removed from and inserted into the holding shell without having to be substantially deformed or stressed in any other way for this purpose. Thus, it is possible to insert and remove the retention insert gently, which can improve the flexibility and lifetime of the connection device.

When the connection device is connected to the implant structure as intended, such that the head of the implant structure is inserted or snapped into the retention insert, radial forces from the head can act on the retention edge of the retention insert. These forces can press the retention edge in the direction of the holding edge of the holding shell, such that the retention edge is moved in the direction of the holding edge. On account of the slit and the opening, the retention edge can thus be moved in a resilient manner in the direction of the holding edge, without being substantially squeezed or similarly deformed. Thus, the retention insert can be firmly connected to the holding shell when the prosthesis structure is connected by means of the connection device to the implant structure. At the same time, the abovementioned spring force from the moved retention edge can act on the head, such that the connection device is clamped on the head.

Preferably, the outer surface of the retention edge of the retention insert is arranged at least partially at a distance from and adjacent to the inner surface of the holding edge of the holding shell, since the outer surface of the retention edge of the retention insert is at least partially more strongly inclined in the direction of a central axis of the connection device than the inner surface of the holding edge of the holding shell. In this connection, the "central axis" corresponds to the mid axis or longitudinal axis of the holding shell or retention insert, which is substantially perpendicular to the respective end face, wherein it can extend in particular perpendicularly through the center point of the respective end face if, for example, these are substantially disk-shaped. In this connection, the term "inclined in the direction of the central axis of the connection device" refers to an inclination of the outer surface of the retention edge or the inner surface of the holding edge relative to the associated end face. This inclination can correlate with an angle between the outer surface of the retention edge or the inner surface of the holding edge and the associated end face, wherein in this case, according to the invention, the angle between the outer surface of the retention edge and the associated end face is smaller than the angle between the inner surface of the holding edge and the associated end face. The mentioned stronger inclinator of the outer surface of the retention edge as compared to the inclination of the inner surface of the holding edge can lead to a space being formed between the outer surface of the retention edge and the inner surface of the holding edge, which space can increase in size starting from the end faces. Thus, the adjacent outer surface of the retention edge and inner surface of the holding edge are at least partially not in contact with each other but instead spaced apart from each other when the retention insert is arranged in the recess of the holding shell and when substantially no radial forces act on the holding edge of the holding shell and on the retention edge of the retention insert.

Preferably, the retention edge of the retention insert has a projection protruding radially from the outer surface of the retention edge of the retention insert, and the holding edge of the holding shell has a corresponding groove extending radially from the inner surface of the holding edge of the holding shell. The groove can in particular extend along substantially the entire circumference of the holding edge. With such a projection and such a corresponding groove, it is possible, in a relatively simple way, to ensure that the retention insert is firmly connected to the holding shell blocked when the retention insert is arranged in the recess of the holding shell and a radial force acts on the holding edge of the holding shell and/or on the retention edge of the retention insert.

The projection of the retention edge of the retention insert can preferably be arranged in the groove of the holding edge of the holding shell such that the retention insert is held releasably in the holding shell when the retention insert is arranged in the recess of the holding shell and when substantially no radial forces act on the holding edge of the holding shell and on the retention edge of the retention insert. In particular, the projection can thus be arranged only partly in the groove when substantially no radial forces act on the holding edge of the holding shell and on the retention edge of the retention insert, such that the retention insert is held sufficiently firmly in the holding shell, so as to be held therein, but nevertheless loosely enough to ensure that it can be easily removed from the holding shell.

Preferably, the projection of the retention edge of the retention insert comprises a substantially plane projection support surface, and the groove of the holding edge of the holding shell comprises a substantially plane groove support surface, wherein a part of the projection support surface bears on a part of the groove support surface when the retention insert is arranged in the recess of the holding shell and when substantially no radial forces act on the holding edge of the holding shell and on the retention edge of the retention insert, and wherein the groove support surface is rounded toward its end directed toward the retention insert and/or the projection support surface is rounded toward its end directed toward the holding shell. In particular, the groove support surface can be rounded away from the projection support surface and the projection support surface can be rounded away from the groove support surface. The projection support surface of the projection of the retention insert can in particular be configured so as to face substantially away from the end face of the retention insert, and the groove support surface of the groove of the holding shell can in particular be configured so as to face substantially toward the end face of the holding shell. With soon a rounded groove support surface and/or projection support surface, it is possible to obtain an appropriate supporting but nonetheless easily releasable connection between retention insert and holding shell.

Preferably, the projection of the retention edge of the retention insert can be arranged in the groove of the holding edge of the holding shell such that the retention insert is connected non-releasably to the holding shell when the retention insert is arranged in the recess of the holding shell and when a radial force acts on the retention edge of the retention insert in the direction of the holding edge of the holding shell and/or acts on the holding edge of the holding shell in the direction of the retention edge of the retention insert. For example, when a force acts on the holding edge in the direction of the retention edge and/or in particular a force acts on the retention edge in the direction of the holding edge, it is possible for the holding edge and the retention edge to be moved relative to each other such that the projection is arranged further or completely in the groove and the retention insert is thus connected permanently or rigidly to the holding shell or blocked. The radial force can be applied to the retention edge and maintained in particular by the head of the implant structure.

Preferably, the holding shell is produced from a biocompatible polymer material, in particular from a polyether ether ketone. Other possible biocompatible materials are polyamides, for example polyhexamethylene adipic acid amide. Connection devices of this kind can be produced easily. Moreover, it is also possible in particular to produce the holding shells from a light-colored, preferably gum colored material, such that the connection device is preferably not readily visible in the mouth of a patient. Moreover, such connection devices can also be used in holistic medicine, in which there are specific requirements regarding the materials and in which, in particular, the use of titanium is not allowed. Alternatively, however, the holding shell can also be produced from titanium.

BRIEF DESCRIPTION OF THE DRAWINGS

The retention insert according to the invention and the connection device according to the invention are described in more detail below on the basis of illustrative embodiments and with reference to the attached drawings, in which.

WAY OF IMPLEMENTING THE INVENTION

Figure 1:
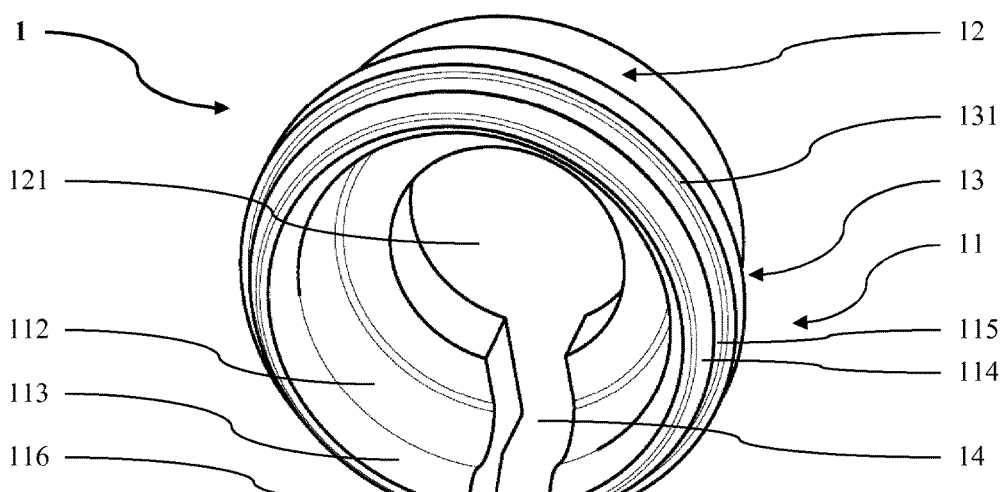
FIG. 1 shows a perspective view of an illustrative embodiment of a retention insert according to the invention.

Certain expressions are used in the following description for practical reasons and are not to be understood in a limiting sense. The words "right""left", "down" and "up" designate directions in the drawing to which reference is made. The expressions "inwardly" and "outwardly" designate directions toward and away from the geometric center point of the illustrated devices and of the stated parts thereof. The terminology includes the words expressly mentioned above, derivations of these, and words of similar meaning.

Figure 2:
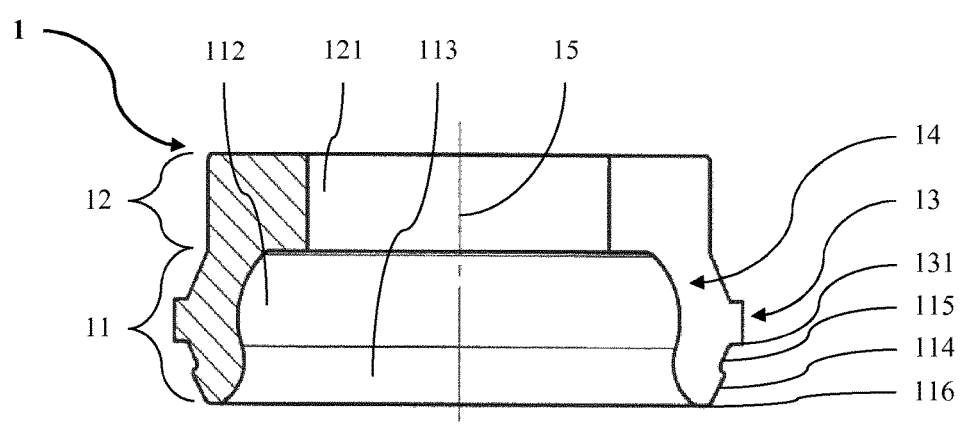
FIG. 2 shows a sectional side view of the retention insert from FIG. 1.

FIG. 1 shows a first illustrative embodiment of a retention insert 1 according to the invention in a perspective view, and FIG. 2 shows a sectional view of the same retention insert 1, wherein the sectional plane runs centrally through a slit. 14, such that the slit 11 is shown to the right in FIG. 2. The substantially pot-shaped retention insert 1 comprises a substantially circular disk-shaped end face 12, and a substantially ring-shaped retention edge 11 protruding at an angle from the circumference thereof. The retention edge 11 has an outer surface 114, and an inner surface 112 opposite the outer surface 114, wherein the inner surface 112 is rounded outwardly toward the open end of the retention insert 1, i.e. toward the end of the retention insert 1 directed away from the end face 12, and thus has a corresponding curved portion 113. The inner surface 112 has an upper, inwardly carved portion with a positive radius of curvature, which merges into the outwardly curved portion 113 with a negative radius of curvature. The inner surface 112 of the retention edge 11 forms, together with an inner surface or lower surface of the end face 12, a recess of the retention insert 1. At the end of the retention edge 11 directed away from the end face 12, the outwardly curved portion 113 merges into a plane portion 116, which forms the end of the retention insert 1 directed away from the end face 12. During use of the retention insert 1, the plane portion 116 can correspond to the apical end of the retention insert 1.

Toward the end of the retention insert 1 directed away from the end face 12, the outer surface 114 of the retention edge 11 is angled with respect to the end face 12, such that it is inclined inwardly in the direction of a central axis 15 of the retention insert 1.

Approximately at the middle of the retention edge 11, a bolt-shaped projection 13 or bar protrudes radially from the outer surface 114 of the retention edge 11 and extends about the entire circumference of the retention edge 11. The projection 13 comprises a plane radial outer face, a plane top face arranged at right angles thereto and directed toward the end face 12, and a plane bottom face which is arranged opposite the top face, is directed away from the end face 12 and defines a projection support surface 131. As can be clearly seen in FIG. 2, the projection 13 extends radially outward beyond the rest of the retention insert 1.

Toward the end of the retention edge 11 directed away from the end face 12, an engagement notch 115 is formed adjacent to the projection 13 on the outer surface 114. By way of the engagement notch 115, the retention insert 1 can be held using a suitable assembly tool, such as is described in WO 2011/027229 A2, for example. In this way, the retention insert 1 can be mounted and manipulated in a preferred manner.

The end face 12 has a central round bore 121 as an opening. The slit 14 as arranged perpendicularly with respect to the end face 12 and is straight. From the plane portion 116 of the retention edge 11, it extends through the entire retention edge 11 and the end face 12 to the bore 121. Thus, the bore 121 is connected to the open end of the retention insert 1 by the slit 14.

The retention insert 1 is produced entire from polyether ether ketone, wherein alternatively another biocompatible polymer material or non-polymer material can be used.

The following statement applies to the entirety of the description below. if, in order to avoid ambiguity in the drawings, a figure contains reference signs that are not mentioned in the directly associated text of the description, then reference is made to the point at which they are explained in previous parts of the description of the figures. Moreover, if reference signs are mentioned in the text of the description directly relating to a figure and are not contained in the associated figure, reference is made to the previous figures.

Figure 3:
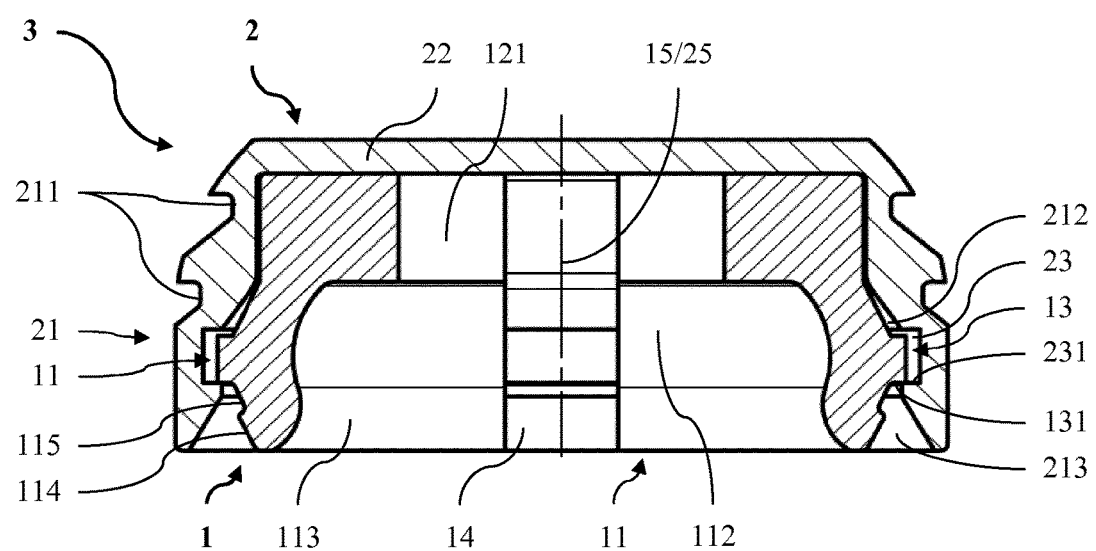
FIG. 3 shows a sectional side view of an illustrative embodiment of a connection device according to the invention with the retention insert from FIG. 1 and with a matrix housing as holding shell.

FIG. 3 shows an illustrative embodiment of a connection device 3 with a matrix housing 2 as holding shell and with the retention insert 1 in cross section, wherein the sectional plane, in comparison to FIG. 2, is turned about the longitudinal axis 15 of the retention insert 1, such that the slit 14 is shown to the front. The substantially pot-shaped matrix housing 2 has a substantially circular disk-shaped closed end face 22 and, protruding at an angle from the circumference thereof, a substantially ring-shaped holding edge 21. The holding edge 21 comprises an inner surface 212, and two notches 211 which are formed on an outwardly curved outer face and are arranged at different heights and extend about the entire circumference of the holding edge 21. Toward the lower open end of the matrix housing 2, the inner surface 212 of the holding edge 21 merges into an outwardly inclined portion 213. From the inner surface 212 of the holding edge 21, a groove 23 is formed in the holding edge 21, which groove 23 comprises an inner surface, a bottom surface arranged at right angles thereto and directed away from the end face 22, and a groove support surface 231 likewise arranged at right angles thereto and directed toward the end face 22. The matrix housing 2 is produced entirely from polyether ether ketone, wherein alternatively another biocompatible polymer materiel or non-polymer material, for example titanium, can also be used.

The retention insert 1 in FIG. 3 has been pushed, with its end face 12 first, through the open end of the matrix housing 2 and into the matrix housing 2, until the end face 12 of the retention insert 1 bears on the end face 22 of the matrix housing 2. During such insertion, the inclined portion 213 of the inner surface 212 of the holding edge 21 serves to center and guide the retention insert 1 with respect to the matrix housing 2. The central axis 15 of the retention insert 1 and a central axis 25 of the matrix housing 2 lie at the same location and together form a central axis of the connection device 3.

Between the inner surface 212 of the holding edge 21 and the outer surface 112 of the retention edge 11, a space between the holding edge 21 and the retention, edge 11 increases toward the bottom or in the direction of the open end of the connection device 1. This space has the effect that the projection 13 of the retention insert 1 lies only partially in the groove 23 of the matrix housing 2. The retention insert 1 is thus held releasably in the matrix housing 2, but the connection device 1 forms one unit.

During use of the connection device 3, the matrix housing 2 is mounted firmly on a prosthesis structure. For this purpose, it can be cast in a synthetic prosthesis material, for example, wherein the notches 211 of the holding edge 21 contribute to a reliable firm connection between matrix housing 2 and prosthesis structure. Moreover, an implant structure with a head designed for a press-fit connection, or patrix head, is implanted in a jaw hone as intended. Before the prosthesis structure is connected to the implant structure, the retention insert 1 is pushed axially into the matrix housing 2 until the retention insert 1 is arranged and held in the matrix housing 2. The retention insert 1 is gently clamped over the projection support surface 131 between the end face 22 of the matrix housing 2 and the groove support surface 231 of the matrix housing 2, such that the retention insert 1 is held in the matrix housing 2 and thus the prosthesis structure.

The prosthesis structure is then arranged on the implant structure, such that the head of the implant structure bears on the retention insert 1 of the connection device 3. Thereafter, the prosthesis structure is pressed onto the implant structure, such that the retention insert 1 is pressed axially onto the head of the implant structure. The connection device 3 is centered by the outwardly curved portion 113 of the retention edge 11. Moreover, a radial force increasing over this outwardly curved portion 113 acts on the retention edge 11, as a result of which the slit 14 and the bore 121 of the retention insert 1 widen, or as a result of which the retention insert 1 is spread open. The retention edge 11 of the retention insert 1 is thus moved in the direction of the holding edge 21 of the matrix housing, such that the projection 13 is arranged in the groove 23 in such a way that the retention insert 1 is connected non-releasably to the matrix housing 2 or blocked.

When the prosthesis structure is placed on the implant structure, the head of the implant structure is snapped into the connection device 3. The head is enclosed in the portion of the inner surface 112 of the retention edge 11 of the retention insert 1 that is curved inwardly with a positive radius of curvature, wherein it is held by the elastic or resilient forces of the retention edge 11 that act in the direction of the central axis and that are induced by the movement of the retention edge 11. Accordingly, the head is held more strongly the greater these elastic forces are. These elastic forces also depend, among other things, on the material from which the retention insert 1 is produced and on the shape of the bore 121 and of the lit 14 in the retention insert 1.

As has been, described above, the retention insert 1 can be modified elastically in terms of its diameter, or spread open, by means of the slit 14 and the bore 121. In addition to the above-described click fit onto a head or patrix head, this also has the effect that, during the insertion of the retention insert 1 into the matrix housing 2, the slit 14 and the bore 121 are briefly narrowed and then expanded again, such that the retention insert 1 can be easily clicked into the matrix housing 2.

Although the invention is illustrated and described in detail on the basis of the figures and the associated description, this illustration and this detailed description are to be understood as illustrative examples and not as limiting the invention. It goes without saying that experts will be able to make changes and adaptations without departing from the scope of the attached claims.

The present disclosure also comprises embodiments with any combination of features that are mentioned or shown above or below in respect of different embodiments. It likewise comprises individual features in the figures, even if they are shown there in connection with other features and/or if they are not mentioned above or below. Moreover, the alternatives of embodiments described in the figures and the description, and individual alternatives of the features thereof, may be excluded from the subject matter of the invention or from the disclosed subject matter. The disclosure comprises embodiments which exclusively comprise the features described in the claims and in the illustrative examples and also those that comprise additional other features.

Moreover, the term "comprise" and derivations thereof do not exclude other elements or steps. Likewise, the indefinite article "a" or "an" and derivations thereof do not exclude a plurality. The functions of several of the features mentioned in the claims can be fulfilled by a unit or a step. The terms "substantially" and "approximately" and the like, in connection with a characteristic or a value, in particular also define exactly this characteristic or exactly this value. The term "approximately", in connection with a given numerical value or range, can relate to a value or range lying within 20%, within 10%, within 5% or within 2% of the given value or range. All the reference signs in the claims are not to be understood as limiting the scope of the claims.

The invention claimed is:

1. A retention insert (1) for connecting a dental prosthesis structure to a dental implant structure or capping structure that has a head designed for a press-fit connection, comprising:
   a substantially circular disk-shaped end face (12), and
   a substantially ring-shaped retention edge (11), which protrudes from the end face (12) and has an outer surface (114),
   wherein the end face (12) and the retention edge (11) form a recess with an inner surface (112), which is designed corresponding to an outer surface of the head of the dental implant structure or capping structure, such that, by arranging the head of the implant structure or capping structure in the recess of the retention insert (1), the retention insert (1) can be snap-fitted onto the head of the implant structure or capping structure, characterized in that the end face (12) has an opening (121), and, starting from an end (116) of the retention edge (11) directed away from the end face (12), a substantially axial slit (14) extends through the retention edge (11) and the end face (12) to the opening (121) of the end face (12).

2. The retention insert (1) as claimed in claim 1, in which the slit (14) is substantially straight.

3. The retention insert (1) as claimed in claim 1, in which the opening (121) of the end face (12) is designed as a bore.

4. The retention insert (1) as claimed in claim 3, in which the bore (121) describes a substantially circular cross section.

5. The retention insert (1) as claimed in claim 1, in which the opening (121) of the end face (12) is slit-shaped.

6. The retention insert (1) as claimed in claim 1, in which the retention edge (11) has a projection (13) protruding substantially radially from the outer surface (114).

7. The retention insert (1) as claimed in claim 1, in which the retention edge (11) has an inner surface (112) which is opposite the outer surface (114) and which is rounded toward the end (116) directed away from the end face (12).

8. The retention insert (1) as claimed in claim 1, which is produced from a biocompatible polymer material.

9. A connection device (3) for connecting a dental prosthesis structure to a dental implant structure or capping structure, comprising a holding shell (2) with an end face (22) and a substantially ring-shaped holding edge (21) protruding therefrom, and a retention insert (1) as claimed in one of the preceding claims, wherein the holding edge (21) and the end face (22) of the holding shell (2) form a recess in which the retention insert (1) can be arranged such that an outer surface (114) of the retention edge (11) of the retention insert (1) lies at least partially at a distance from and adjacent to an inner surface (212) of the holding edge (21) of the holding shell (2) when the retention insert (1) is arranged in the recess of the holding shell (2) and when substantially no radial forces act on the holding edge (21) of the holding shell (2) and on the retention edge (11) of the retention insert (1).

10. The connection device (3) as claimed in claim 9, in which the outer surface (114) of the retention edge (11) of the retention insert (1) is arranged at least partially at a distance from and adjacent to the inner surface (212) of the holding edge (21) of the holding shell (2), since the outer surface (114) of the retention edge (11) of the retention insert (1) is at least partially more strongly inclined in the direction of a central axis (15, 25) of the connection device (3) than the inner surface (212) of the holding edge (21) of the holding shell (2).

11. The connection device (3) as claimed in claim 9, in which the retention edge (11) of the retention insert (1) has a projection (13) protruding radially from the outer surface (114) of the retention edge (11) of the retention insert (1), and the holding edge (21) of the holding shell (2) has a corresponding groove (23) extending radially from the inner surface (212) of the holding edge (21) of the holding shell (2).

12. The connection device (3) as claimed in claim 11, in which the projection (13) of the retention edge (11) of the retention insert (1) can be arranged in the groove (23) of the holding edge (21) of the holding shell (2) such that the retention insert (1) is held releasably in the holding shell (2) when the retention insert (1) is arranged in the recess of the holding shell (2) and when substantially no radial forces act on the holding edge (21) of the holding shell (2) and on the retention edge (11) of the retention insert (1).

13. The connection device (3) as claimed in claim 11, in which the projection (13) of the retention edge (11) of the retention insert (1) has a substantially plane projection support surface (131), and the groove (23) of the holding edge (21) of the holding shell (2) has a substantially plane groove support surface (231), wherein a part of the projection support surface (131) bears on a part of the groove support surface (231) when the retention insert (1) is arranged in the recess of the holding shell (2) and when substantially no radial forces act on the holding edge (21) of the holding shell (2) and on the retention edge (11) of the retention insert (1), and wherein the groove support surface (231) is rounded toward its end directed toward the retention insert (1) and/or the projection support surface (131) is rounded toward its end directed toward the holding shell (2).

14. The connection device (3) as claimed in claim 11, in which the projection (13) of the retention edge (11) of the retention insert (1) can be arranged in the groove (23) of the holding edge (21) of the holding shell (2) such that the retention insert (1) is connected non-releasably to the holding shell (2) when the retention insert (1) is arranged in the recess of the holding shell (2) and when a radial force acts on the retention edge (11) of the retention insert (1) in the direction of the holding edge (21) of the holding shell (2) and/or acts on the holding edge (21) of the holding shell (2) in the direction of the retention edge (11) of the retention insert (1).

15. The connection device (3) as claimed in claim 11, in which the holding shell (2) is produced from a biocompatible polymer material.

* * * * *